United States Patent [19]

Carson

[11] Patent Number: 4,652,584

[45] Date of Patent: Mar. 24, 1987

[54] ACETYLENIC PHENOXYPROPANOL DERIVATIVES AND PHARMACEUTICAL COMPOSITIONS FOR THE TREATMENT OF HYPERTENSION

[75] Inventor: John R. Carson, Norristown, Pa.

[73] Assignee: McNeilab, Inc., Fort Washington, Pa.

[21] Appl. No.: 630,796

[22] Filed: Jul. 13, 1984

[51] Int. Cl.$^4$ ................ A61K 31/275; A61K 31/135; C07C 95/08; C07C 121/60
[52] U.S. Cl. .............................. 514/524; 260/501.17; 514/522; 514/546; 514/605; 514/618; 514/619; 514/620; 514/630; 514/650; 514/652; 549/551; 549/553; 549/556; 549/557; 549/559; 549/560; 558/413; 558/414; 558/422; 560/138; 560/250; 560/251; 564/99; 564/162; 564/165; 564/167; 564/220; 564/337; 564/338; 564/349; 564/350; 564/351
[58] Field of Search .......... 260/465 D, 465 E, 501.17; 560/138, 250, 251; 514/522, 524, 546, 605, 618, 619, 620, 630, 650, 652; 549/551, 553, 556, 557, 559, 560; 558/413, 414, 422; 564/99, 162, 165, 167, 220, 337, 338, 349, 350, 351

[56] References Cited

U.S. PATENT DOCUMENTS

| | | | |
|---|---|---|---|
| 3,590,084 | 6/1971 | Peperkamp et al. | 260/570.7 |
| 3,914,432 | 10/1975 | Koppe et al. | 424/304 |
| 3,959,338 | 5/1976 | Koppe et al. | 260/465 E |
| 4,010,158 | 3/1977 | Koppe et al. | 260/253 |
| 4,412,856 | 11/1983 | Brunner et al. | 71/121 |

FOREIGN PATENT DOCUMENTS 2503222 7/1976 Fed. Rep. of Germany .
813564 12/1981 South Africa .

OTHER PUBLICATIONS

Michael T. Cox, et al., Journal of Medicinal Chemistry, 1978, vol. 21, No. 2, pp. 182–188.
V. Machacek, et al., Coll. Czechoslov. Chem. Commun., vol. 37, 3073, (1972).
Kenkichi Sonogashira, et al., Tetrahedron Letters, No. 50, pp. 4467–4470, (1975).
R. D. Stephens, et al., Journal of Organic Chemistry 28, pp. 3313–3315, (1963).

Primary Examiner—Dolph H. Torrence
Attorney, Agent, or Firm—David J. Levy

[57] ABSTRACT

Phenoxypropanol derivatives having a 2-acetylenic moiety on the phenyl group thereof of the following formula (I):

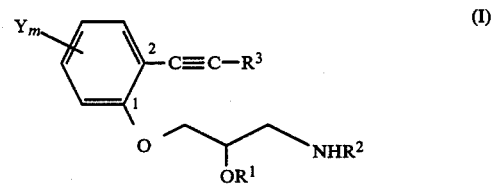

and their use as anti-hypertensives, e.g. in man. Also part of the invention are pharmaceutical compositions and intermediates used in the synthesis.

20 Claims, No Drawings

ACETYLENIC PHENOXYPROPANOL DERIVATIVES AND PHARMACEUTICAL COMPOSITIONS FOR THE TREATMENT OF HYPERTENSION

The present invention comprises certain 1-phenoxy-2-propanols wherein the phenyl group is substituted at the 2-position with an acetylenic group. Such compounds are useful in the treatment of hypertension.

At pages 182–188 of the Journal of Medicinal Chemistry, Vol. 21, No. 2 (1978) M. T. Cox et al., describes a class of linked aryl aryloxypropanols which do not show any significant $\beta$-blocking activity. Two of the listed compounds are linked via an acetylenic moiety.

SUMMARY OF THE INVENTION

Acetylenes of the formula (I):

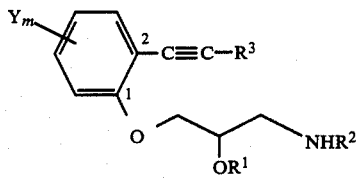

wherein Y may be a variety of substituents optionally attached at 1, 2 or 3 of the open positions, $R^1$ is hydrogen or alkanoyl, $R^2$ is a particular alkyl or phenylethyl moiety and $R^3$ is chosen from disclosed moieties. Such acetylenes are useful as anti-hpertensives. Also part of the invention are novel intermediates and pharmaceutical compositions.

DETAILED DESCRIPTION OF THE INVENTION

Compounds of the invention are of the following formula (I):

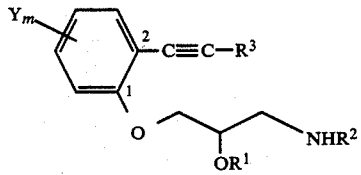

wherein
Y is alkyl, cycloalkyl, fluoro, chloro, bromo, hydroxy, trifluoromethyl, alkoxy, alkylthio, alkenyl, alkynyl, alkenyloxy, alkynyloxy, alkoxyalkyl, alkylthioalkyl, alkanoyl, alkanoyloxy, alkanoylamino, alkanoylaminoalkyl, carboxamido, carboxamidoalkyl, N-alkylcarboxamido, N,N-dialkylcarboxamido, phenyl or alkylsulfonylamino; m is 0, 1, 2 or 3:
$R^1$ is hydrogen or alkanoyl;
$R^2$ is iso-propyl, tert-butyl, sec-butyl, phenylethyl, 2-phenyl-1-methylethyl, (substituted phenyl)ethyl or 2-(substituted phenyl)-1-methylethyl wherein the substituion on said phenyl groups is independently one or two of fluoro, chloro, bromo, hydroxy, methoxy, ethoxy, methylthio, ethylthio, carboxamido, methyl and ethyl; and
$R^3$ is hydrogen, alkyl, cycloalkyl, phenyl or phenyl independently substituted by one, two or three of hydroxy, alkyl, alkoxy, alkylthio, fluoro, chloro, bromo, amino, alkylamino, dialkylamino, alkanoylamino, cyano, carboxamido, N-alkylcarboxamido, N,N-dialkylcarboxamido, N,N-dialkylaminoalkyl and trifluoromethyl,
and the pharmaceutically acceptable acid-addition salts thereof.

Y in particular, is alkyl of about 1 to 6 carbons such as methyl, ethyl or iso-propyl; cycloalkyl of about 3 to 7 carbons such as cyclopropyl; fluoro; chloro; bromo; hydroxy; trifluoromethyl, e.g. 5-trifluoromethyl; alkoxy of about 1 to 6 carbons, such as methoxy, ethoxy or iso-propoxy, e.g. 5-methoxy; alkylthio of about 1 to 6 carbons, such as methylthio or ethylthio; alkenyl of about 2 to 6 carbons, such as vinyl or allyl; alkynyl of about 2 to 6 carbons such as 2-propargyl; alkenyloxy of about 2 to 6 carbons, such as vinyloxy; alkynyloxy of about 2 to 6 carbons; alkoxyalkyl of about 2 to 8 carbons, such as ($C_{1-4}$alkoxy)$C_{1-4}$alkyl, e.g. methoxymethyl; alkanoyl of about 2 to 6 carbons, such as acetyl; alkanoyloxy of about 2 to 6 carbons such as acetoxy; alkanoylamino of 2 to 6 carbons, such as acetamido; alkanoylaminoalkyl of about 3 to 10 carbons, such as ($C_{2-6}$alkanoyl)amino($C_{1-4}$alkyl), e.g. acetylaminomethyl; carboxamido, i.e. —CONH$_2$, e.g., 4-carboxamido; carboxamidoalkyl of about 2 to 6 carbons, such as —CH$_2$CH$_2$CONH$_2$; N-alkylcarboxamido of about 2 to 6 carbons, such as —CONHCH$_3$; N,N-dialkylcarboxamido of about 3 to 11 carbons, such as those having about 1 to 5 carbons in each alkyl group, e.g. —CON(CH$_3$)$_2$; phenyl or alkylsulfonylamino of about 1 to 4 carbons, e.g. —NHSO$_2$CH$_3$.

Values for m include 0, 1, 2 and 3 and in particular 1 or 2, e.g. wherein a single Y group is at the 4- or 5-position.

$R^1$, in particular, is hydrogen; or alkanoyl of about 2 to 7 carbons such as acetyl or 2,2-dimethylpropanoyl.

$R^2$, in particular, is iso-propyl; tert-butyl; sec-butyl; phenethyl; 2-phenyl-1-methylethyl; (substituted phenyl)ethyl; or 2-(substituted phenyl)-1-methylethyl wherein the substitution on each of such phenyl rings is one or two of chloro or methoxy, such as two methoxy groups or two chloro groups, e.g. at the 3- and 4-positions of the phenyl ring.

$R^3$, in particular, is hydrogen; alkyl of about 1 to 6 carbons, e.g., methyl, ethyl or n-butyl; cycloalkyl of about 3 to 7 carbons, such as cyclopropyl or cyclohexyl; phenyl; or phenyl substituted by 1 to 3, same or different, of hydroxy, alkyl of about 1 to 6 carbons such as methyl or ethyl, alkoxy of about 1 to 6 carbons such as methoxy or ethoxy, alkylthio of about 1 to 6 carbons such as methylthio or ethylthio, fluoro, chloro, bromo, amino, alkylamino of about 1 to 4 carbons such as methylamino, dialkylamino of about 2 to 8 carbons such as di($C_{1-4}$alkyl)amino, e.g. dimethylamino or N-methyl-N-ethylamino, alkanoylamino of about 2 to 6 carbons such as acetylamino or propanoylamino, cyano, carboxamido of the formula —CONH$_2$, N-alkylcarboxamido of about 2 to 6 carbons such as —CONHCH$_3$, N,N-dialkylcarboxamido of about 3 to 11 carbons such as N,N-di($C_{1-5}$)carboxamido, e.g. —CON(CH$_3$)$_2$, N,N-dialkylaminoalkyl of about 1 to 4 carbons in each alkyl of the dialkyl portion and about 1 to 6 carbons in the alkylene, e.g., ($C_{1-4}$alkyl)$_2$N($C_{1-6}$alkyl)-, such as dimethylaminoethyl and N-methyl-N-ethylaminopropyl, and trifluoromethyl. The substitution on the phenyl ring is, in particular, a single methoxy, chloro, dimethylamino, acetylamino, cyano or carboxamido group at the 3- or 4-position of the phenyl ring, e.g. 4-(dimethylamino)-phenyl.

Compounds of formula (I) and other compounds of the invention may exist in various isomeric forms, e.g., in view of the presence of an asymmetric carbon, e.g. the carbon attached directly to the $OR^1$ group. It is understood that the present invention includes all such individual optical and geometric isomers and their racemates. Also within the scope of the invention are compounds of the invention in the form of hydrates and other solvate forms. "Alkyl" as used herein is indicative of straight and branched chain alkyl.

Representative salts of compounds of formula (I) which may be used include those made with acids such as hydrochloric, hydrobromic, hydroiodic, perchloric sulfuric, nitric, a phosphoric, acetic, propionic, glycolic, lactic, pyruvic, malonic, succinic, maleic, fumaric, malic, tartaric, citric, benzoic, cinnamic, mandelic, methanesulfonic, ethanesulfonic, hydroxyethanesulfonic, benzenesulfonic, p-toluenesulfonic, cyclohexanesulfonic, salicylic, p-aminosalicylic, 2-phenoxybenzoic, 2-acetoxybenzoic or a salt made with saccharin.

Particular compounds of the invention of formula (I) include the following, prepared as described hereafter in Examples 1 through 20 respectively:

1-[(1,1-dimethylethyl)amino]-3-[2-(phenylethynyl)-phenoxy]-2-propanol;
1-[(1,1-dimethylethyl)amino]3-[2-(phenylethynyl)-phenoxy]-2-propyl-2,2-dimethylpropanoate;
1-[(1-methylethyl)amino]-3-[2-(phenylethynyl)-phenoxy]-2-propanol;
1-[[2-(3,4-dimethoxyphenyl)ethyl]amino]-3-[2-(phenylethynyl)phenoxy]-2-propanol;
1-[1,1-dimethylethyl)amino]-3-[5-methoxy-2-(phenylethynyl)phenoxy]-2-propanol;
1-[[2-(3,4-dimethoxyphenyl)ethyl]amino]-3-[5-methoxy-2-(phenylethynyl)phenoxy]-2-propanol;
1-[[2-(3,4-dimethoxyphenyl)ethyl]amino]-3-[2-[[4-(dimethylamino)phenyl]ethynyl]-5-methoxy-phenoxy]-2-propanol;
N-[3-[[2-[3-[[2-(3,4-dimethoxyphenyl)ethyl]amino]-2-hydroxypropoxy]-4-methoxyphenyl]ethynyl]-phenyl]acetamide;
1-[[2-(3,4-dimethoxyphenyl)ethyl]amino]-3-[5-methoxy-2-[(4-methoxyphenyl)ethynyl]phenoxy]-2-propanol;
1-[[2-(3,4-dichlorophenyl)ethyl]amino]-3-[5-methoxy-2-(phenylethynyl)phenoxy]-2-propanol;
1-[[2-(3,4-dimethoxyphenyl)-1-methylethyl]amino]-3-[5-methoxy-2-(phenylethynyl)phenoxy]-2-propanol;
1-[(1,1-dimethylethyl)amino]-3-[2-(4-chlorophenylethynyl)phenoxy]-2-propanol;
1-[(1,1-dimethylethyl)amino]-3-[2-(4-methoxy-phenylethynyl)phenoxy]-2-propanol;
4-[2-[3-[(1,1-dimethylethyl)amino]-2-hydroxypropoxy]phenylethynyl]benzonitrile;
4-[[2-[3-[(1,1-dimethylethyl)amino]-2-hydroxypropoxy]phenyl]ethynyl]benzamide;
1-[(1,1-dimethylethyl)amino]-3-[2-[(4-dimethylaminophenyl)ethynyl]phenoxy-2-propanol;
1-[(1,1-dimethylethyl)amino]-3-[2-(1-hexynyl)-phenoxy]-2-propanol;
N-[3-[[2-[3-[(1,1-dimethylethyl)amino]-2-hydroxypropoxy]phenyl]ethynyl]phenyl]acetamide;
4-[2-hydroxy-3-[(1,1-dimethylethyl)amino]propoxy]-3-(phenylethynyl)benzamide; and
1-[(1,1-dimethylethyl)amino]-3-[(2-phenylethynyl)-5-trifluoromethyl)phenoxy]-2-propanol.

Compounds of formula (I) may be prepared according to the following reaction scheme which is described in detail below:

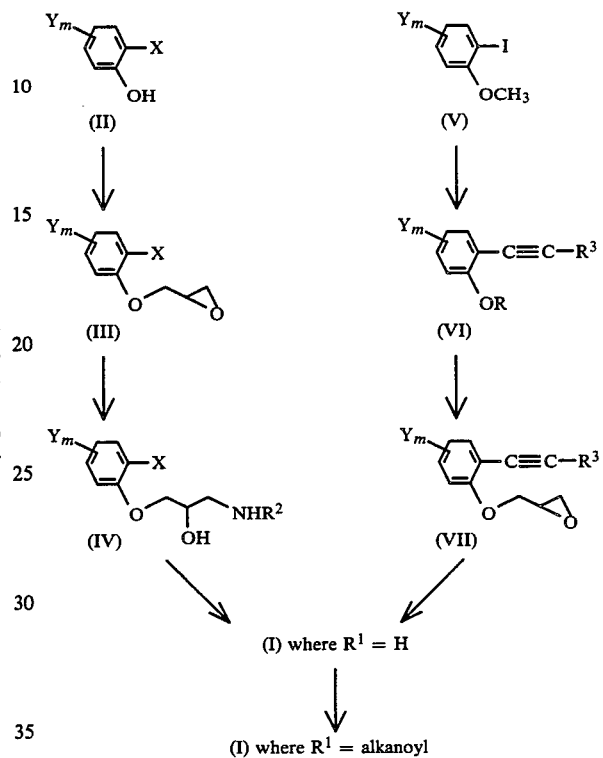

Firstly, a phenol (II) wherein X is hydrogen is halogenated (X=Br or I) in the ortho position to give an ortho halophenol (II) wherein X is Br or I. In order to induce the halogen to enter into the ortho position, the phenolate anion is the species which is halogenated, see Machacek, Sterba and Valter, Collection Czechoslav. Chem. Commun., 37, 3703 (1972). The halogenation can be carried out by generating the phenolate anion, for instance with sodium hydride, an alkali metal alkoxide or an alkali metal hydroxide followed by adding a halogenating agent such as iodine or bromine. The halogenation is preferably carried out in an inert solvent such as toluene, benzene or a halocarbon. The halogenation may be performed over a temperature range of −40° to 50° C. When the position para to the phenol group is blocked by the presence of a Y substituent, the ortho halogenation may be carried out on the phenol itself by halogenating agents such as iodine monochloride, iodine-nitric acid, iodine-mercuric oxide, bromine, pyridinimum bromide perbromide or cupric bromide. The ortho halophenol (II) where X is Br or I is then alkylated with epichlorohydrin in the presence of base to give the epoxide (III). The bases employed may be alkali metal hydride, alkali metal alkoxides or alkali metal carbonates. The reaction may be carried out at ambient to elevated temperatures for example from about 25° to about 125° C. A period of heating may be required to convert the intermediate chlorohydrin to epoxide (III) following the disappearance of (II). The reaction may be performed in any solvent generally used for alkylation reactions, for example lower alkanols, aromatic solvents or ethers. Especially advantageous due to higher rates of reaction are the dipolar aprotic solvents such as DMF, DMSO, sulfolane and methyl ethyl ketone. The opening of the epoxide (III) by amines $R^2NH_2$ to give ortho halophenoxy propanolamines (IV) is carried out by heating the reactants in a lower alkanol or a dipolar aprotic solvent, e.g. DMF, DMSO, dimethyl acetamide or sulfolane, at 50° to 150° C. The coupling of an orthohalophenoxypropanolamine (IV) with an arylethyne or 1-alkyne to give an orthoaryl ethynyl or ortho-1-alkynylphenoxy propanolamine (I) where $R^1$ is hydrogen is carried out by the method of Sonogashira et al, see Tetrahedron Lett. 4467 (1975). For the preparation of the compounds of formula (I) wherein $R^3$ is hydrogen, the corresponding compound wherein $R^3$ is 1-hydroxy-1-methylethyl may be prepared by reacting a compound of formula (IV) with 2-methyl-2-butynol in the presence of Pd(O). The thus-produced compound of formula (I) where $R^3$ = 1-hydroxy-1-methylethyl may then be treated with base to yield a compound of formula (I) where $R^3$ = H. For example, the compound of formula (I) wherein $R^3$ is 1-hydroxy-1-methylethyl may be heated at 50°-140° C. in an inert solvent such as toluene, xylene or chloroform in the presence of concentrated aqueous sodium hydroxide in the presence of a quaternary ammonium phase transfer catalyst such as, for example, tetrabutylammonium chloride. The halophenoxypropanolamine (IV) and the acetylene are stirred at ambient to elevated temperature e.g. 25°-110° C. with a palladium catalyst (0.1 to 5 mole %) such as $(Ph_3P)_4Pd(O)$, $(Ph_3P)_2P(II)Cl_2$ or $(Ph_3P)_2Pd(II)OAc$ in an amine solvent such as triethylamine, diethylamine, piperidine or pyrrolidine in the presence of a catalytic quantity (0.5–5 mole %) of a cuprous salt. If desired, a copper (I) acetylide may be performed instead of adding a catalytic quantity of cuprous salt.

O-Acyl derivatives (I) where $R^1$ is alkanoyl may be prepared by acylation of (I) where $R^1$ is hydrogen under acidic conditions. For example, treatment of an acid addition salt of a compound of formula (I), $R^1$ = H, with an alkanoic acid anhydride using the corresponding alkanoic acid as the solvent at elevated temperatures, e.g. 40°-80° C., affords an O-acyl derivative of formula (I), $R^1$ = alkanoyl.

Second, compounds of formula (I) may be prepared by an alternative route in which the acetylene group is introduced on the phenoxy moiety prior to the attachment of the propanolamine side chain. An orthohaloanisole (V) is coupled with an acetylene of formula $HCCR^3$ to give an ortho(aliphatic or aromatic)ethynylanisole (VI), R=$CH_3$. The palladium catalyzed coupling method of Sonogashira et al. may also be used to effect this transformation under the conditions described for the conversion of (IV) to (I) $R^1$=H. Alternatively, the haloanisole may be coupled with a copper-(I)acetylide as described by Stevens and Castro in the Journal of Organic Chem., 28, 3313 (1963). These reactants are heated together at the reflux temperature of the solvent, preferably pyridine or DMF. The O-methoxyphenylacetylene (VI), R=$CH_3$ is demethylated to give the o-hydroxyphenylacetylene (VI), R=H, by heating under reflux with trimethylsilyl iodide in an inert solvent such as benzene, toluene, xylene, chloroform or 1,2-dichloroethane. Cleavage of the intermediate trimethylsilyl ether may be accomplished by stirring the reaction mixture with methanol. The conversion of formula (VI), R=H, to formula (VII) and formula (VII) to (I) may be carried out as described above for the analogous transformations, of formula (II) X=Br or I, to formula (III) and formula (III) to (IV), respectively.

Acetylenes used in the above-described processes of the formula HC≡C—$R^3$ may be obtained from Farchen Laboratories of 4702 East 355th Street, Willoughby, Ohio 44094. Arylethynes for reaction with the compound of formula (IV) in the above reaction scheme may be prepared by the method of Ames et al as described in Synthesis, 364 (1981). Treatment of the aryl iodide with $PdCl_2[(Ph)_3P]_2$ or $Pd(OAc)_2[(Ph)_3P]_2$ and 2-methyl-3-butyn-2-ol affords an acetylenic carbinol which may be cleaved with an alkali metal hydroxide to give the arylethyne as exemplified in the Examples below. The arylethyne may be converted to the corresponding cuprous arylacetylide by treatment with cuprous iodide in ammonium hydroxide solution.

The activity of compounds of formula (I) for the treatment of hypertension may be determined using the Spontaneously Hypertensive Rat (SHR) test as described below.

In this test, the arterial pressure of adult spontaneously hypertensive rats (Charles River) is monitored directly via an aortic cannula. The SH rats are anesthetized with an inhalation anesthetic (ether). The left carotid artery is isolated and cannulated. The tip of the cannula is advanced to the aorta and the cannula is exteriorized behind the neck at the level of the scapula. Animals are placed in individual cages and allowed to recover from the anesthetic and are kept unrestrained. The arterial cannula is connected to the pressure transducer which is attached to the recorder. The test compounds are administered to at least 3 rats at doses selected in the range of 0.1 to 100 mg/kg of body weight by intraperitoneal (i.p.) or oral (p.o.) routes of administration. The arterial pressure and heart rate are monitored for a minimum of 24 hours. A test compound is considered to be active as an antihypertensive agent if the mean arterial pressure (MAP) indicates a fall of >15 mm of Hg. Each animal serves as its own control. In the SHR test, the compound produced in Example 16 showed a maximum change in mean arterial blood pressure of a fall of 69 mm of Hg when administered at 30 mg per kg of body weight, p.o.

In addition to their utility in the treatment of hypertension, the compounds of formula (I) are useful in the treatment of the symptoms of angina pectoris by virtue of their ability to dilate coronary arteries. Often, peripheral arteries are also dilated by compounds which dilate coronary arteries and thus, this test is also useful for predicting activity as an antihypertensive. Compounds of the invention were tested in this regard in the "Langendorff's Isolated Heart" model as generally described in "Pharmaceutical Experiments on Isolated Preparations", Staff of the Department of Pharmacology, University of Edinbourgh, 2nd Ed., Churchill, Livingston, N.Y. (1970) pages 112–119. In this test, the compound of the invention of formula (I) produced in Example 6b. required a 0.04 μM concentration to elicit a 30% increase in flow.

A third system for determining the ability of compounds of the invention to act as anti-hypertensives is the Evaluation of Potential Beta Adrenergic Blocking Activity. Potential beta blocking activity was evaluated in two in vitro tests. The potential Beta-1 antagonistic activity was evaluated using isoproterenol induced tachycardia in guinea pig atrial pairs (a.). Beta-2 activity was evaluated using blockade of isoproterenol-induced relaxation of acetylcholine contracted tracheal rings (b.). Beta-2 activity as an antagonist is indicative of the undesirable side effect of the constriction of bronchial smooth muscle.

a. In vitro guinea pig atrial pairs: Female guinea pigs weighing 250–500 g were anesthetized in a carbon dioxide chamber, the chest was opened and the heart was carefully removed. The heart was then placed in cold Krebs-bicarbonate buffer in a Petri dish and the atria were carefully dissected. The atria were mounted in 50 ml baths in Krebs-bicarbonate buffer at 35° C., and airated with 95% $O_2$/5% $CO_2$. Contractions were monitored using a Narco isometric force transducer under 1.0 g tension. Rate was monitored using the output from the force transducer using a Narco Biotach. Recordings were made using a Narco Physiograph. Studies were done by doing multiple concentration response curves to isoproterenol using at least three concentrations of tests compounds. $ED_{50}$'s for isoproterenol tachycardia were constructed for the means of at least three experiments. $ED_{50}$'s were calculated using a relative potency program in the DEC 1011 (RELPOT) along with relative potencies.

The competitiveness of the antagonism, if any was determined by Schild plots using the Log(dose ratio-1) vs. -Log (concentration of antagonist). Propranolol was used as a positive control and potencies of test compounds were compared to it. The product of Example 18 had a $pA_2$ of 8.15±0.16, with the $pA_2$ for propranolol being 8.69±0.18.

b. In vitro guinea pig tracheal rings: Guinea pigs were sacrificed in a carbon dioxide chamber and the trachea removed carefully. The trachea was cleaned and placed in a Petri dish with Kreb's Bicarbonate buffer. Rings of cartilage with attached smooth muscle were cut and chains of two or three rings were made by tying the rings together using silk thread. The chain was mounted in a 10 ml organ bath immersed in a water bath kept at 35° C. The chain was attached to a Narco isometric force transducer and kept under 1 g tension. In order to evaluate the effects of the experimental compounds as Beta-2 antagonists the trachea were contracted with 1 μg/ml acetylcholine and increasing concentrations of isoproterenol were added at 5 minute intervals until the trachea was completely relaxed. Increasing doses of the test compound were given 5 minutes after acetylcholine and 5 minutes prior to the addition of cumulative doses of isoproterenol. Means and standard error from at least 3 experiments were calculated and $ED_{50}$'s for isoproterenol were determined using a relative potency program (RELPOT) on the DEC 1011. Competitiveness was determined as with the guinea pig atria pair study. Propranolol was used as a positive control and as the standard of reference for all active test compounds.

A fourth test for determining the ability of compounds of the invention to act as anti-hypertensive agents is the Calcium Entry Blockade test using vascular smooth muscle. Male New Zealand White Rabbits (H.A.R.E.) (body weight = 1.8–2.4 kg) are sacrificed by cervical fracture and the thoracic aorta is removed under standard HEPES buffer. The aorta is rinsed in several changes of standard HEPES and cleared of extraneous tissue. Scissors are used to segment the aorta into 3 mm rings (approximately 12 rings/aorta). For studies of tension, individual rings are equilibrated for one hour in standard HEPES buffer under isometric tension (1 g) between two parallel horizontal wires. For calcium influx studies, the following procedures are executed. After completion of the one-hour equilibration period, the test is begun. To baths containing vascular rings to be tested for the effects of an experimental agent on calcium influx in the basal state (absence of an agonist), the agent dissolved in 20 μl of vehicle (PEG 300 or $H_2O$) is added and a parallel vehicle bath is started receiving the vehicle alone. To baths containing vascular rings to be tested for the effects of an experimental agent on calcium influx during agonist stimulation, the experimental agent is added in a fashion identical to that described for the basal test and parallel vehicle baths are also initiated. All baths are allowed to equilibrate for 30 minutes. Subsequently, to basal test baths, 20 μl of $H_2O$ is added; to baths receiving KCl, 400 μl of $H_2O$ containing 60 mM KCl is added; to baths receiving NE, 20 μl of $H_2O$ containing 10 μM NE is added. All baths are allowed to equilibrate for an additional 28½ minutes. At this time, all rings in each bath are quickly removed from their respective bath, quickly but gently blotted and transferred to a bath containing an identical solution but also containing $^{45}Ca$(20 μl, 2.5 μCi/ml; New England Nuclear, Boston, MA). Rings are allowed exposure to the radiolabelled solution for exactly three minutes. Subsequently, the rings are removed, blotted to remove excess fluid, and placed in predesignated test tubes containing ice cold wash solution where they are allowed to equilibrate for 45 minutes in the presence of vigorous bubbling with 100% $O_2$. Subsequently, individual rings are removed, blotted, weighed (Mettler Balance model AE 163), and placed in a scintillation vial containing 2 ml of 7.5 mM EDTA solution (pH = 10.0). Vials are held overnight in darkness. This procedure has been shown to totally displace tissue bound calcium into the solution phase. Subsequently, 13 ml of Beckman HP scintillation fluid is added to each vial with shaking, vials are cleaned, and counted using a Beckman LS 6800 liquid scintillation counter. Blanks containing solutions alone are simultaneously counted to provide background information.

For tension studies, the following procedures are executed. After completion of the one-hour equilibration period, the test is begun. At this time, all tissue tensions are adjusted mechanically back to the 1 gram baseline. Subsequently, all tissue baths receive either KCl (60 mM) plus phentolamine (1 μM) in 400 μl $H_2O$ or NE (10 μM in 20 μl PEG 300). All rings are allowed to develop tension for exactly 30 minutes. Subsequently, the bathing solution is removed and replaced immediately with normal HEPES buffer without experimental agents and the tension response is allowed to "wash out". Two subsequent washes are introduced at 10 minute intervals before the rings can achieve the prestimulation baseline tone. Subsequently, the experimental drug or vehicle is added to each bath and the rings are allowed to equilibrate for exactly 30 minutes. Finally, the agonist challenge is repeated as described previously in the presence of the experimental agent. Cellular calcium values are calculated using the following formula: total cellular calcium = $^{45}Ca$ retained/$^{45}Ca$ sp.act.(wt) where total cellular calcium is the total amount of calcium ions in the tissue at the end of the experimental procedure, $^{45}Ca$ sp.act. the specific activity of the labelled calcium in the wash solution, and wt = weight of the vessel ring in kgs.

In view of testing carried out as described above on compounds of the invention, two of the best compounds of the invention are believed to be the compounds produced in Examples 1d. and 16, i.e., of the formula (I) wherein m is 0; $R^1$ is hydrogen; $R^2$ is tertiary butyl; and $R^3$ is phenyl or 4-(dimethylamino)phenyl.

Some of the compounds of the invention possess both β-blocking and calcium entry blockade activities as indicated in the above tests, e.g., the product of Example 1d. It has been speculated that such a combination of modes of action may be a desirable feature of an antihypertensive medication.

For the treatment of hypertension or angina, compounds of the present invention of the formula (I) may be administered orally or parenterally in a pharmaceutical composition comprising about 1 to 2,000 mg, preferably about 30 to 400 mg of one or more of the acetylene compounds per day for an average adult human depending on the activity of the particular compound chosen. The dosage may be divided into 1 to 4 unit dosage forms per day. While the therapeutic methods of the invention are most useful for human subjects in need of alleviation of hypertension or angina, the compounds may be administered to other mammals at comparable dosages per weight of the subject.

Pharmaceutical compositions containing the acetylene compounds of the present invention of formula (I) or an acid addition salt thereof as the active ingredient may be prepared by intimately mixing the acetylene compound with a pharmaceutical carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed, including liquid carriers such as water, glycols, oils, alcohols and the like for oral liquid preparations such as suspensions, elixers and solutions; and solid carriers such as starches, sugars, kaolin, calcium stearate, ethyl cellulose, etc., including materials which function as lubricants, binders, disintegrating agents and the like for powders, capsules and tablets. Because of their ease in administration, tablets and capsules represent the most advantageous oral dosage form. These compositions employ solid pharmaceutical carriers such as the aforementioned starches, sugars, kaolin and the like, generally with a lubricant such as calcium stearate. It is especially advantageous to formulate the aforementioned pharmaceutical compositions in dosage unit form for ease of administration and uniformity of dosage. The term "dosage unit form" as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets, capsules, pills, powder packets, wafers, teaspoonful, tablespoonful and the like, and segregated multiples thereof.

Also part of the present invention are the pharmaceutical compositions, e.g. as described above, and methods for the treatment of hypertension and angina using such compositions as well as novel intermediates used in their synthesis as described, particularly those of the formula (VII).

In the following Examples and throughout the specification, the following abbreviations may be used: E (trans); Z (cis); bp (boiling point); mp (melting point); g (grams); ml (milliliters); μl (microliters); glc (gas liquid chromatography); N (normal); M (molar); μM (micromolar); mM (millimolar); THF (tetrahydrofuran); MeOH (methanol); DMF (dimethylforamide); mmoles (millimoles); mg (milligrams); mm (millimeters); p.o. (per os); and C,H,N, etc. (the chemical symbols for the elements). Unless otherwise indicated, all temperatures are reported in degrees centigrade (°C.) and all pressures in mm of mercury.

EXAMPLE A 1-(3,5-Dichlorophenyl)-3-methyl-1-butyn-3-ol

A mixture of 25.5 g (0.094 mole) of 3,5-dichloroiodobenzene, 550 ml dry triethylamine, 12 g (0.14 mole) of 2-methyl-2-hydroxy-3-butyne, 0.42 g (0.0019 mole) palladium (II) acetate, and 1 g (0.0038 mole) of triphenylphosphine was heated to reflux under nitrogen for four hours. The resulting mixture was cooled, diluted with ether and washed with two 500-ml portions of 3N hydrochloric acid. The ether layer was separated, dried over anhydrous magnesium sulfate, and evaporated in vacuo to yield the crude product as an oily residue. The purified product was obtained by distillation to yield 7.95 g, bp 115°–125° C./0.0001 mm.

EXAMPLE B 1,3-Dichloro-5-ethynylbenzene

A mixture of 7.95 g (0.0655 mole) of 1-(3,5-dichlorophenyl)-3-methyl-1-butyn-3-ol and 30 g of sodium hydroxide in 150 ml of dry toluene was heated to reflux with stirring for 3.5 hours. The toluene was removed in vacuo to yield a brown solid residue. The residue was triturated with hexane and the resulting hexane solution washed with aqueous sodium thiosulfate solution. The hexane layer was separated and evaporated in vacuo to yield the crude product. Recrystallization from hexane yielded 4.15 g of pure product, mp 80°–81.5° C.

EXAMPLE 1 a. 1-Methoxy-2-(phenylethynyl)benzene

A mixture of 187.2 g (0.80 mole) of o-iodoanisole and 184.1 g (1.12 mole) of cuprous phenylacetylide in 2.4 liters of pyridine was refluxed overnight under nitrogen. The next day an additional 9.0 g (0.055 mole) of cuprous phenylacetylide was added and the reaction mixture refluxed overnight. The pyridine was evaporated, the reaction mixture taken up in ether and washed with water, 3N HCl, brine, and dried with MgSO₄. The ether was evaporated in vacuo to give 186.0 g of black liquid. Distillation at 118°–125° C., 0.005 mm Hg gave 120.0 g (72% yield) of 1-methoxy-2-(phenylethynyl)benzene.

b. 2-(Phenylethynyl)phenol

A mixture of 162.2 g (0.779 mole) of 1-methoxy-2-(phenylethynyl)benzene and 122 ml (0.857 mole) of iodotrimethylsilane in 310 ml of chloroform was heated under reflux for one week. The reaction mixture was cooled to 25° C., poured into methanol and stirred for one hour. The methanol was evaporated keeping the temperature below 40° C. The reaction was taken into ether and washed with 5% sodium bisulfite, saturated sodium bicarbonate, brine, and dried (MgSO₄). The ether was evaporated in vacuo to give 176.8 g of semisolid material. Two recrystallizations from methylcyclohexane gave 37.5 g (33%) of 2-(phenylethynyl)phenol, mp 65°–66° C.

c. [[2-(phenylethynyl)phenoxyl]methyl]oxirane

A mixture of 37.5 g (0.193 mole) of 2-(phenylethynyl)phenol, 75.5 ml (0.965 mole) epichlorohydrin, and 80.0 g (0.579 mole) of anhydrous potassium carbonate in 250 ml of methyl ethyl ketone was refluxed overnight. The solvent was evaporated in vacuo and the residue taken into ether, washed with water and brine, dried with MgSO$_4$, and evaporated to give 47.7 g (99% yield) of a semi-solid [[2-(phenylethynyl)phenoxy]methyl]oxirane.

d. 1-[(1,1-Dimethylethyl)amino]-3-[2-(phenylethynyl)phenoxy]-2-propanol Hydrochloride A mixture of 9.0 g (0.036 mole) of [[2-(phenylethynyl)phenoxy]methyl]oxirane and 37.8 ml (0.360 mole) of t-butylamine in 45 ml of sulfolane was added to an autoclave and heated on a steam bath for 2.5 hrs. The reaction mixture was taken into ether, washed six times with water, once with brine and dried (K$_2$CO$_3$). The ether was evaporated in vacuo to give 10.1 g of oil. The oil was dissloved in ether, ethereal HCl added, and 6.0 g of white solid was filtered. One recrystallization from isopropanol gave 5.6 g (43% yield) of 1-[(1,1-dimethylethyl)amino]-3-[2-(phenylethynyl)phenoxy]-2-propanol hydrochloride, mp 165°–166° C. The product of Example 1d. demonstrated significant blockade of the potentialdependent calcium channel and related vascular tone in the isolated rabbit thoracic aorta. At 1.0 and 10.0 μM, this compound caused dose dependent inhibition of KCl stimulated effects on calcium influx and tone, reducing these by 100% at 10 μM. This compound had no effect on norepinephrine-induced calcium influx or tone.

EXAMPLE 2

1-[(1,1-Dimethylethyl)amino]-3-[2-(phenylethynyl)phenoxy]-2-propyl 2,2-Dimethylpropanoate Hydrochloride A solution of 6.0 g (0.017 mole) 1-[(1,1-dimethylethyl)amino]-3-[2-(phenylethynyl)phenoxy]-2-propanol, the product of Example 1d. and 17.1 g pivalic acid was heated under N$_2$ to 50° C. and 4.1 ml (0.020 mole) of pivalic anhydride was added. After three hours the temperature was raised to 75° C. and after four hrs another 10 g of pivalic acid was added to thin the solution. After five hours the reaction was cooled to 25° C. and chloroform was added. After stirring for one hour the chloroform was evaporated and the reaction mixture taken up in ether. The resulting precipitate was filtered to give 6.25 g of a white solid. Two recrystallizations from 2-propanol gave 5.78 g (76% yield) of 1-[(1,1-dimethylethyl)amino]-3-[2-(phenylethynyl)phenoxy]-2-propyl 2,2-dimethylpropanoate hydrochloride, mp 197°–198° C.

EXAMPLE 3

1-[(1-Methylethyl)amino]-3-[2-(phenylethynyl)phenoxy]-2-propanol Hydrochloride A mixture of 5.5 g (0.022 mole) of [[2-(phenylethynyl)phenoxy]methyl]oxirane, the product of Example 1c. and 18.7 ml (0.220 mole) of isopropylamine in 27.5 ml of sulfolane was added to an autoclave and heated for 2.5 hrs on a steam bath. The reaction was poured into ether, washed five times with water, once with brine and dried (K$_2$CO$_3$). The ether was evaporated in vacuo to give 6.0 g of oil. The oil was dissolved in ether and 2-propanol and ethereal HCl added. The resultant precipitate was filtered to give 5.47 g of white solid. Three recrystallizations from ethanol gave 4.5 g (59%) of white solid, 1-[(1-methylethyl)amino]-3-[2-(phenylethynyl)phenoxy]-2-propanol hydrochloride, mp 154.5°–156° C.

EXAMPLE 4

1-[[2-(3,4-Dimethoxyphenyl)ethyl]amino]-3-[2-(phenylethynyl)phenoxy]-2-propanol (E)-2-Butenedioate (2:1)

A mixture of 12.0 g (0.048 mole) of [[2-(phenylethynyl)phenoxy]methyl]oxirane, the product of Example 1c., 9.7 ml (0.058 mole) of homoveratrylamine and 60 ml of sulfolane, was heated for three hours on a steam bath. The reaction mixture was poured into ether, washed five times with water, once with brine and dried (K$_2$CO$_3$). The ether was evaporated in vacuo to give 18.5 g of an oil which was combined with 2.6 g of fumaric acid in acetone, cooled and filtered to give 10.4 g of solid material. Two recrystallizations in 95% ethanol gave 9.0 g (38%) of 1-[[2-(3,4-dimethoxyphenyl)ethyl]amino]-3-[2-(phenylethynyl)phenoxy]-2-propanol (E)-2-butenedioate (2:1), mp 154°–155.5° C.

EXAMPLE 5 a. 2-Iodo-5-methoxyphenol

To a round bottom flask under nitrogen was added 8.4 g (0.174 mole) of 50% NaH in oil. The NaH was washed twice with hexane, cooled to 0° C. in ice, and 20.0 g (0.161 mole) of m-methoxyphenol in 200 ml of toluene was added with stirring. After the evolution of hydrogen was complete 34.1 g (0.134 mole) of iodine dissolved in 600 ml of toluene was added over 30 minutes. A 100 ml portion of toluene was used to wash in the remaining iodine. The reaction was stirred for 1½ hrs., ether was added and the organic layer washed with 3N HCl, water, sodium thiosulfate, brine and dried with MgSO$_4$. The solvent was evaporated in vacuo and the residue crystallized from 1:1 toluene:methylcyclohexane to give 24.1 g of green solid. The green solid was stirred with charcoal in methanol for ½ hr., the solution filtered, and evaporated in vacuo, and the resulting residue recrystallized in 1:1 toluene:methylcyclohexane to give 19.8 g (55% yield) of 2-iodo-5-methoxyphenol, mp 70°–72.5° C.

b. [(2-Iodo-5-methoxyphenoxy)methyl]oxirane

A 5.0 g (0.02 mole) sample of 2-iodo-5-methoxyphenol was added in portions to a suspension of 1.01 g (0.021 mole) of 50% sodium hydride (from which the oil had been removed by washing with hexane) in 40 ml of dry DMF. The resulting solution was cooled to 5° C. and 9.14 g (0.099 mole) of epichlorohydrin was added. The mixture was heated at 60° C. for 15 minutes. The mixture was cooled and filtered through diatomaceous earth. The solvent was evaporated in vacuo from the filtrate. The residue was taken up in ether, the ether washed with water and brine, dried (MgSO$_4$) and the solvent evaporated in vacuo to give 5.72 g (93% yield) of [(2-iodo-5-methoxyphenoxy)methyl]oxirane as a brown oil.

c.
1-[(1,1-Dimethylethyl)amino]-3-[2-iodo-5-methoxyphenoxy]-2-propanol Hydrochloride A solution of 20 g of [(2-iodo-5-methoxyphenoxy)methyl]oxirane (0.065 mole) and 35 ml (0.33 mole) of t-butylamine in 40 ml of sulfolane was heated at 90° C. in an autoclave for 3 hr. The reaction was cooled and the t-butylamine evaporated in vacuo. The residue was dissolved in ether and the solution washed with water and brine and dried ($K_2CO_3$). Ethereal hydrogen chloride and a little MeOH were added and the precipitate collected in two crops. There was obtained 19.25 g of crystalline 1-[(1,1-dimethylethyl)amino]-3-[2-iodo-5-methoxyphenoxy]-2-propanol hydrochloride, mp 195°–198° C.

d.
1-[(1,1-Dimethylethyl)amino]-3-[5-methoxy-2-(phenylethynyl)phenoxy]-2-propanol (E)-2-Butenedioate (2:1)

A solution of 10 g (26.4 mmoles) of 1-[(1,1-dimethylethyl)amino]-3-[2-iodo-5-methoxyphenoxy]-2-propanol, 5.0 ml (34.6 mmole) of phenylacetylene, 0.093 g (0.132 mmoles) of $(Ph_3P)_2PdCl_2$, and 0.05 g (0.264 mmole) of copper (I) iodide in 65 ml of triethylamine was stirred at room temperature under $N_2$ for 18 hr. Ether was added. The organic layer was washed with water and brine, dried ($K_2CO_3$) and the solvent evaporated in vacuo. A fumarate salt was prepared from the residue using MeOH as the solvent. It was recrystallized from MeOH to give 6.0 g (55% yield) of crystalline 1-[(1,1-dimethylethyl)amino]-3-[5-methoxy-2-(phenylethynyl)phenoxy]-2-propanol (E)-2-butendioate (2:1), mp 187°–189° C.

EXAMPLE 6
a.
1-[[2-(3,4-Dimethoxyphenyl)ethyl]amino]-3-(2-iodo-5-methoxyphenoxy)-2-propanol A solution of 5.0 g (0.016 mole) of [(2-iodo-5-methoxyphenoxy)methyl]oxirane, the product of Example 5b. and 3.25 g (0.0179 mole) of homoveratrylamine in 10 ml of sulfolane was heated at 60°–70° C. for 18 hr. Water was added and the precipitate which formed was collected by filtration. It was recrystallized from acetonitrile to give 7.0 g (87% yield) of crystalline 1-[[2-(3,4-dimethoxyphenyl)ethyl]amino]-3-(2-iodo-5-methoxyphenoxy)-2-propanol, mp 83°–88° C.

b.
1-[[2-(3,4-Dimethyoxyphenyl)ethyl]amino]-3-[5-methoxy-2-(phenylethynyl)phenoxy]-2-propanol (E)-2-Butenedioate (2:1)

A solution of 9.0 g (18.5 mmole) of 1-[[2-(3,4-dimethoxyphenyl)ethyl]amino]-3-(2-iodo-5-methoxyphenoxy)-2-propanol, 3.46 ml (24.2 mmoles) of phenylacetylene, 0.065 g (0.0925 mmoles) of $(Ph_3P)_2PdCl_2$ and 0.035 g (0.185 mmoles) of copper (I) iodide in 50 ml of triethylamine was stirred for 66 hr under $N_2$. Ether was added. The organic layer was washed with water and brine, dried ($K_2CO_3$) and the solvent evaporated in vacuo. A fumarate salt was prepared from 95% ethanol as solvent. It was recrystallized twice from 2-propanol/MeOH to give 4.6 g (46% yield) of crystalline 1-[[2-(3,4-dimethoxyphenyl)ethyl]-amino]-3-[5-methoxy-2-(phenylethynyl)phenoxy]-2-propanol (E)-2-butendioate (2:1), mp 146°–148° C.

The product of Example 6b. was an active coronary vasodilator in the isolated Langendorff test but had no effect on spontaneous rate or contractile force. The compound was tested over the concentration range of 0.01 to 3.0 $\mu M$. It induced active vasodilation (+39%) at 0.1 $\mu M$.

EXAMPLE 7
1-[[2-(3,4-Dimethoxyphenyl)ethyl]amino]-3-[2-[[4-(dimethylamino)phenyl]ethynyl]-5-methoxyphenoxy]-2-propanol (E)-2-butenedioate hydrate (4:3:1)

Using the procedure of Example 6b. and employing an equivalent quantity of 4-dimethylaminophenylacetylene in place of phenylacetylene, there was obtained the title compound as the product, mp 159°–161° C.

EXAMPLE 8
a. N-(3-Ethynylphenyl)acetamide

A 30.0 g (0.256 mole) sample of 3-aminophenylacetylene was cooled at ice bath temperature and 27.0 ml (0.282 mole) of acetic anhydride was added dropwise. The ice bath was removed and the mixture stirred for 30 min. The mixture was diluted with ether and the resulting solution washed with water, $NaHCO_3$ solution and brine. The organic phase was dried ($K_2CO_3$) and the solvent evaporated in vacuo. The crystalline residue was recrystallized from $CHCl_3$-hexane to give 60.7 g (89% yield) of crystalline N-(3-ethynylphenyl)acetamide, mp 94°–96° C.

b.
N-[4-[[2-[3-[[2-(3,4-dimethoxyphenyl)ethyl]amino]-2-hydroxypropoxy]-4-methoxyphenyl]ethynyl]phenyl]acetamide (E)-2-Butenedioate (2:1)

Using the procedure of Example 6b. and employing an equivalent quantity of N-(3-ethynylphenyl)acetamide in place of phenylacetylene there was obtained the title compound as the product, mp 196.5°–197.5° C.

EXAMPLE 9
1-[[2-(3,4-dimethoxyphenyl)ethyl]amino]-3-[5-methoxy-2-[(4-methoxyphenyl)ethynyl]phenoxy]-2-propanol (E)-2-Butenedioate hydrate (4:3:1)

Using the procedure of Example 6b. and employing an equivalent quantity of 4-methoxyphenylacetylene in place of phenylacetylene, there was obtained the title compound as the product, mp 154°–156° C.

EXAMPLE 10
a.
1-[[2-(3,4-dichlorophenyl)ethyl]amino]-3-(2-iodo-5-methoxyphenoxy)-2-propanol Hydrochloride (1:1)

Using the procedure of Example 6a. and employing an equivalent quantity of 3,4-dichlorophenethylamine in place of homoveratrylamine there was obtained the title compound as the product, mp 174.5°–176.5° C.

b.
1-[[2-(3,4-dichlorophenyl)ethyl]amino]-3-[5-methoxy-2-(phenylethynyl)phenoxy]-2-propanol Hydrochloride Using the procedure of Example 6b. and employing an equivalent quantity of 1-[[2-(3,4-dichlorophenyl)ethyl]amino]-3-(2-iodo-5-methoxyphenoxy)-2-propanol in place of 1-[[2-(3,4-dimethoxyphenyl)ethyl]amino]-(2- iodo-5-methoxyphenoxy)-2-propanol, there was obtained the title compound as the product, mp 186°–187° C.

EXAMPLE 11 a.

1-[[2-(3,4-Dimethoxyphenyl)-1-methylethyl]amino]-3-(2-iodo-5-methoxyphenoxy)-2-propanol A solution of 5.6 g (0.018 mole) of [(2-iodo-5-methoxyphenoxy)methyl]oxirane, the product of Example 5b. and 3.25 g (0.016 mole) of 2-(3,4-dimethoxyphenyl)-alphamethylethylamine in 15 ml of sulfolane was heated at 80° C. for one hour and at 110° for six hours. The mixture was dissolved in ether and the ether washed with water and brine. The ether layer was dried ($K_2CO_3$) and the solvent evaporated in vacuo. The residue was flash chromatographed on $SiO_2$ using $MeOH:CHCl_3$, 1:30 as the eluant. The major compound bearing fractions were pooled and the solvent evaporated in vacuo. There was obtained 5.9 g (71% yield) of 1-[[2-(3,4-dimethoxyphenyl)-1-methylethyl]amino]-3-(2-iodo-5-methoxyphenoxy)-2-propanol as a yellow oil.

b.

1-[[2-(3,4-Dimethoxyphenyl)-1-methylethyl]amino]-3-[5-methoxy-2-(phenylethynyl)phenoxy]-2-propanol (E)-2-Butenedioate A solution of 5.1 g (10.2 mmoles) 1-[[2-(3,4-dimethoxyphenyl)-1-methylethyl]amino]-3-(2-iodo-5-methoxyphenoxy)-2-propanol, 1.6 ml (14.25 mmoles) of phenylacetylene, 0.036 g (0.051 mmole) of $(Ph_3P)_2PdCl_2$, and 0.184 g (0.01 mole) of copper (I) iodide in 30 ml of triethylamine was stirred for 18 hr under $N_2$ at room temperature. The reaction mixture was dissolved in ether and washed with water and brine. The solution was dried ($K_2CO_3$) and the solvent evaporated in vacuo. A fumarate salt was prepared from MeOH-ether solvent. It was recrystallized from MeOH-ether to give 3.2 g (60% yield) of 1-[[2-(3,4-dimethoxyphenyl)-1-methylethyl]amino]-3-[5-methoxy-2-(phenylethynyl)phenoxy]-2-propanol (E)-2-butenedioate, mp 155°–160° C.

EXAMPLE 12 a. [(2-iodophenoxy)methyl]oxirane

To a round bottom flask under $N_2$ was added 4.56 g (0.095 mole) of 50% NaH in oil. The NaH was washed twice with hexane, then 220 ml of DMF was added. Aliquots of 20.0 g (0.091 mole) of o-iodophenol were added over 15 minutes then 30.0 ml (0.450 mole) of epichlorohydrin was added and the solution heated to 70° C. After two hours the reaction was evaporated in vacuo, taken into $CHCl_3$, washed with 10% NaOH, water, and brine and dried with $MgSO_4$. The solvent was evaporated in vacuo to give 24.93 g of crude product. Distillation at 110°–114° C., 0.05 mm Hg gave 20.0 g (80.0%) of [(2-iodophenoxy)methyl]oxirane.

b.

1-[(1,1-Dimethylethyl)amino]-3-(2-iodophenoxy)-2-propanol Hydrochloride

A solution of 30.0 g (0.108 mole) of [(2-iodophenoxy)methyl]oxirane and 110 ml (1 mole) of t-butylamine in 62 ml of sulfolane was heated in an autoclave for two hours. The excess t-butylamine was evaporated in vacuo. The residue was dissolved in ether and the ether solution washed with water and brine. The solution was dried ($K_2CO_3$), and the solvent was evaporated in vacuo. A hydrochloride salt was prepared by adding ethereal hydrogen chloride to an ether solution of the residue. There was obtained 25 g (53% yield) of crystalline 1-[(1,1-dimethylethyl)amino]-3-(2-iodophenoxy)-2-propanol hydrochloride, mp 184° to 185° C.

c.

1-[(1,1-Dimethylethyl)amino]-3-[2-(4-chlorophenylethynyl)phenoxy]-2-propanol (E)-2-Butenedioate A mixture of 8.73 g (25 mmoles) of 1-[(1,1-dimethylethyl)amino]-3-(2-iodophenoxy)-2-propanol, 7.47 g (37.5 mmoles) of copper (I) 4-chlorophenylacetylide and 0.175 g (0.25 mmole) of $(Ph_3P)_2PdCl_2$, in 100 ml of triethylamine was stirred under Ar for 72 hr at 25° C. It was heated at 50° for 6 hr. An additional 0.175 g of $(Ph_3P)_2PdCl_2$ was added. The reaction was stirred for 16 hr. An additional 0.175 g of $(Ph_3P)_2PdCl_2$ and 0.75 g of copper (I) 4-chlorophenylacetylide in 25 ml of triethylamine was added. The mixture was heated for 4 hr. The mixture was dissolved in $CH_2Cl_2$ and the resulting solution washed with concentrated ammonia and water, dried ($K_2CO_3$) and the solvent evaporated in vacuo. The residue was dissolved in MeOH and filtered. A 2.58 g sample of fumaric acid was added and the solvent evaporated in vacuo. The residue crystallized from $CH_3CN$. It was recrystallized from $MeOH/CH_3CN$ to give 4.9 g (41% yield) of crystalline 1-[(1,1-dimethylethyl)amino]-3-[2-(4-chlorophenylethynyl)phenoxy]-2-propanol (E)-2-butenedioate, mp 184°–185° C.

EXAMPLE 13

1-[(1,1-Dimethylethyl)amino]-3-[2-(4-methoxyphenylethynyl)phenoxy]-2-propanol (E)-2-Butenedioate (3:2)

A mixture of 8.03 g (0.023 mole) of 1-[(1,1-dimethylethyl)amino]-3-(2-iodophenoxy)-2-propanol, the product of Example 12b., 4.5 g (0.023 mole) of copper (I) 4-methoxyphenylacetylide, and 0.161 g (0.23 mmole) of $(Ph_3P)_2PdCl_2$ was stirred under Ar for 18 hr at 25°. It was heated at 45° C. for 2 hr. An additional 0.67 g (3.3 mmole) of copper (I) 4-methoxyphenylacetylide was added. The reaction was heated at 45° for one hour. The reaction mixture was dissolved in $CH_2Cl_2$ and washed with concentrated ammonia and water. The solution was dried ($K_2CO_3$) and the solvent evaporated in vacuo. The residue was dissolved in MeOH and 2.40 g of fumaric acid added. The MeOH was evaporated in vacuo and the residue crystallized from $CH_3CN$. The solid was recrystallized twice from $MeOH/CH_3CN$ and once from MeOH/2-propanol to give 4.06 g (41% yield) of crystalline 1-[(1,1-dimethylethyl)amino]-3-[2-(4-methoxyphenylethynyl)phenoxy]-2-propanol (E)-2-butenedioate (3:2), mp 200°–201° C.

EXAMPLE 14

4-[2-[3-](1,1-Dimethylethyl)amino]-2-hydroxypropoxy]phenylethynyl]benzonitrile (E)-2-Butenedioate Hydrate (50:25:17)

A solution of 6.6 g (19 mmoles) of 1-[(1,1-dimethylethyl)amino]-3-(2-iodophenoxy)-2-propanol, the product of Example 12b., 2.5 g (19.7 mmoles) of p-cyanophenylacetylene, 0.44 g (0.38 mmole) of $(Ph_3P)_4Pd$ and 0.07 g (0.78 mmole) of copper (I) iodide in 40 ml of deoxygenated triethylamine and 20 ml of deoxygenated THF was stirred under nitrogen for 18 hr. A precipitate was removed by filtration and discarded. The solvent was evaporated from the filtrate in vacuo. Trituration of the residue with ether gave a crystalline solid which was collected by filtration. Evaporation of the ether filtrate gave a second crop of crystalline product. The combined crystalline material was dissolved in MeOH and fumaric acid (0.5 equivalent) was added. There was obtained 5.6 g (75%) of crystalline 4-[2-[3-[(1,1-dimethylethyl)amino]-2-hydroxypropoxy]phenylethynyl]benzonitrile (E)-2-butenedioate hydrate (50:25:17), mp 198°–200° C.

EXAMPLE 15

4-[[2-[3-[(1,1-Dimethylethyl)amino]-2-hydroxypropoxy]phenyl]ethynyl]benzamide

A solution of 11.5 ml (31.5 mmoles) of 3N NaOH solution was added to a solution of 5.8 g (15.3 m moles) of 4-[2-[3-[(1,1-dimethylethyl)amino]-2-hydroxypropoxy]phenylethynyl]benzonitrile, the product of Example 14 in 50 ml of 95% ethanol. The mixture was heated under reflux for 30 min. The solution of 25 ml of 95% ethanol and 5.0 ml of 3N aqueous NaOH was added. The mixture was heated under reflux for 15 min. The solution was cooled and the solid collected by filtration. The solid was recrystallized from 95% ethanol to give 4.38 g of 4-[[2-[3-[(1,1-dimethylethyl)amino]-2-hydroxypropoxy]phenyl]ethynyl]benzamide, mp 199°–201° C.

EXAMPLE 16

1-[(1,1-Dimethylethyl)amino]-3-[2-[(4-dimethylaminophenyl)ethynyl]phenoxy]-2-propanol (E)-2-Butenedioate (1:1)

Using the procedure of Example 14 and employing an equivalent quantity of 4-dimethylaminophenylacetylene in place of 4-cyanophenylacetylene, there was obtained the title compound of the product, mp 174°–175° C. The product of Example 16 did not exhibit typical calcium channel blocking activity in the isolated rabbit thoracic aorta. At 10 μM this compound reduced KCl-dependent contractile activity by 50% and had no effect on KCl-dependent calcium flux. However, this compound reduced norepinephrine-induced calcium flux without changing tension.

EXAMPLE 17

1-[(1,1-Dimethylethyl)amino]-3-[2-(1-hexynyl)phenoxy]-2-propanol (E)-2-Butenedioate (8:7)

A solution of 9.03 g (26.6 mmole) of 1-[(1,1-dimethylethyl)amino]-3-(2-iodophenoxy)-2-propanol, the product of Example 12b., 4.00 ml (34.6 mmoles) of 1-hexyne, 0.093 g (0.133 mmole) of (Ph$_3$P)$_2$PdCl$_2$, and 0.051 g (0.266 mmole) of copper (I) iodide in 70 ml of triethylamine was stirred under Ar at 25° C. for 16 hr. An additional 4 ml of 1-hexyne, 0.093 g of (Ph$_3$P)$_2$PdCl$_2$, and 0.051 g of copper (I) iodide were added. The mixture was stirred for 20 hr under Ar at 25° C. The mixture was heated at 50° C. for 5 hr. The reaction was diluted with ether. The solution was washed with water and brine, dried (K$_2$CO$_3$) and the solvent evaporated in vacuo. The residue was dissolved in MeOH and 3.07 g of fumaric acid was added. The MeOH was evaporated in vacuo. The residue was crystallized from methyl ethyl ketone. A total of 6.5 g of crystals were obtained in two crops. The solid was recrystallized twice from CH$_3$CN to give 4.99 g (46% yield) of white crystalline 1-[(1,1-dimethylethyl)amino]-3-[2-(1-hexynyl)phenoxyl]-2-propanol (E)-2-butenedioate (8:7), mp 132°–134° C.

EXAMPLE 18

N-[3-[[2-[3-[(1,1-Dimethylethyl)amino]-2-hydroxypropoxy]phenyl]ethynyl]phenyl]acetamide 4-methylbenzene sulfonate A solution of 9.00 g (25.6 mmoles) of 1-[(1,1-dimethylethyl)amino]-3-(2-iodophenoxy)-2-propanol, the product of Example 12b., 5.32 g (33.3 mmoles) of N-(3-ethynylphenyl)acetamide, the product of Example 8a., 0.09 g (0.13 mmole) of (Ph$_3$P)$_2$PdCl$_2$ and 0.049 g (0.26 mmole) of copper (I) iodide in 17 ml of THF and 50 ml of triethylamine was stirred at 25° C. under Ar for 66 hr. The solvent was evaporated in vacuo. The residue was dissolved in CH$_2$Cl$_2$ and the solution washed with water. The CH$_2$Cl$_2$ solution was decanted from a foamy precipitate, dried (K$_2$CO$_3$) and the solvent evaporated in vacuo. The residue was dissolved in MeOH and 5.25 g of p-toluenesulfonic acid hydrate added. The MeOH was evaporated in vacuo and the residue crystallized from CH$_3$CN. The solid was recrystallized twice from CH$_2$CN to give 3.63 g (26% yield) of white crystalline N-[3-[[2-[3-[(1,1-dimethylethyl)amino]-2-hydroxypropoxy]phenyl]ethynyl]phenyl]acetamide 4-methylbenzenesulfonate, mp 154°–156° C.

EXAMPLE 19 a. 4-Hydroxy-3-iodobenzamide

A sample of 47 g (0.29 mole) of ICl was added to a solution of 40 g (0.29 mole) of 4-hydroxybenzamide in 400 ml of MeOH and 800 ml of acetic acid in the absence of light. The mixture was stirred for 70 hr under N$_2$ at 25° C. A precipitate was collected by filtration. The filtrate was diluted with water and a second crop of crystals collected by filtration. A third crop was obtained by evaporation of solvent from the second filtrate. The combined solids were recrystallized from 95% ethanol. The solid which precipitated and was collected (28 g). It was largely diiodinated material. The filtrate was evaporated in vacuo and the residue recrystallized from MeOH. The precipitated solid was collected by filtration (2.0 g). It was again diiodinated material. The filtrate was concentrated to dryness in vacuo to give 23 g (30% yield) of brownish crystalline 4-hydroxy-3-iodobenzamide, mp 90°–95° C.

b. 3-Iodo-4-(oxiranylmethoxy)benzamide

A solution of 10.0 g (0.038 mole) of 4-hydroxy-3-iodobenzamide in 40 ml of dry DMF was added to a suspension of 0.04 mole of sodium hydride (from 1.9 g of 50% sodium hydride which had been washed free of oil with hexane) in 60 ml of dry DMF at 25° under N$_2$. When bubbling ceased, 30 ml (0.38 mole) of epichlorohydrin was added dropwise. The mixture was heated at 70° C. for 90 min and allowed to stand at 25° C. for 16 hr. The mixture was filtered. The filtrate was concentrated to dryness in vacuo. The residue was dissolved in CH$_2$Cl$_3$. The solution was washed with water and brine, dried (MgSO$_4$) and the solvent evaporated in vacuo. The residue was recrystallized from CH$_2$Cl$_2$/hexane to give 5.4 g (50% yield) of 3-iodo-4-(oxiranylmethoxy)benzamide, mp 149°–151° C.

c. 4-[2-Hydroxy-3-[(1,1-dimethylethyl)amino]propoxy]-3-iodobenzamide

A solution of 3.75 g (0.01 mole) of 3-iodo-4-(oxiranylmethoxy)benzamide and 10.5 ml (0.1 mole) of t-butylamine in 7 ml of sulfolane was heated at 90° C. in an autoclave. After 2 hr the vessel was cooled and the t-butylamine was evaporated in vacuo. The residue was crystallized from $CH_2Cl_2/CH_3CN$ to give 4.0 g (100% yield) of 4-[2-hydroxy-3-[(1,1-dimethylethyl)amino]-propoxy]-3-iodobenzamide as a white crystalline solid, mp 111°–114° C.

d.
4-[2-Hydroxy-3-[(1,1-dimethylethyl)amino]propoxy]-3-(phenylethynyl)benzamide Hydrate (4:1)

A solution of 3.75 g (9.57 mmoles) of 4-(2-hydroxy-3-[(1,1-dimethylethyl)amino]propoxy]-3-iodobenzamide, 1.6 ml (14.35 mmole) of phenylacetylene, 0.036 g (0.048 mmole) of $(Ph_3P)_2PdCl_2$ and 0.018 g (0.0957 mmole) of copper (I) iodide in 20 ml of triethylamine and 10 ml of THF (which had been deoxygenated by admission of $N_2$) was stirred at 25° C. under $N_2$ for one hour. It was heated at 60° for 3 hr. The precipitate which formed on cooling was collected by filtration and dried in vacuo. A fumarate salt was prepared in MeOH solvent and ether was added. A total of 3.0 g was collected by filtration in two crops. The solid was stirred with dilute NaOH and the crystalline free base was collected by filtration. The solid was recrystallized from $CH_3CN$ to give 1.2 g of crystalline 4-[2-hydroxy-3-[(1,1-dimethylethyl)amino]propoxy]-3-(phenylethynyl)benzamide hydrate (4:1), mp 167°–169° C.

EXAMPLE 20 a. 2-Iodo-5-trifluoromethylphenol

To a round bottom flask under $N_2$ was added 14.2 g (0.296 mole) of sodium hydride, 50% in oil. The NaH was washed twice with hexane, and 33.15 g (0.205 mole) of m-trifluoromethylphenol in 1 liter of toluene was added. After five minutes 51.9 g (0.205 mole) of iodine was added all at once, and the solution allowed to stir overnight. The reaction was poured into 3N HCl, ether added, and the separated organic layer washed with water, brine and dried with $MgSO_4$. The solvent was evaporated in vacuo to give 60.3 g (100% yield) of 2-iodo-5-trifluoromethylphenol, mp 36°–38° C.

b. [2-Iodo-5-trifluoromethylphenoxy)methyl]oxirane

A sample of 20 g (0.069 mole) of 2-iodo-5-trifluoromethylphenol was added in portions to a suspension of 0.07 mole of NaH (from 3.36 g of 50% NaH which had been washed free of oil with hexane) in 150 ml of dry DMF under $N_2$. When gas evolution had ceased, a 27 ml (0.347 mole) sample of epichlorohydrin was added dropwise at 5° C. The mixture was heated at 60° C. for 3 hr and allowed to stand at 25° C. for 16 hr. A precipitate was removed by filtration. The filtrate was concentrated to dryness in vacuo. The residue was taken up in ether, washed with water and brine, dried ($K_2CO_3$) and the solvent evaporated in vacuo to give 20.4 g (86% yield) of [(2-iodo-5-trifluoromethylphenoxy)methyl]oxirane as an oil.

c.
1-[(1,1-Dimethylethyl)amino]-3-[2-iodo-5-(trifluoromethyl)phenoxy]-2-propanol Hydrochloride A solution of 10.0 g (0.029 mole) of [(2-iodo-5-trifluoromethylphenoxy)methyl]oxirane and 30 ml (0.29 mole) of t-butylamine in 20 ml of sulfolane was heated at 90° in an autoclave for 2 hr. The excess t-butylamine was evaporated in vacuo. The residue was dissolved in ether, washed with water and brine, dried ($K_2CO_3$) and concentrated to dryness in vacuo. The residue was dissolved in ether and ethereal hydrogen chloride was added. The precipitate was collected by filtration and dried. There was obtained 8.9 g (67% yield) of white crystalline 1-[(1,1-dimethylethyl)amino]-3-[2-iodo-5-(trifluoromethyl)phenoxyl]-2-propanol hydrochloride, mp 174°–178° C.

d.
1-[(1,1-Dimethylethyl)amino]-3-[(2-phenylethynyl)-5-(trifluoromethyl)phenoxy]-2-propanol (E)-2-Butenedioate (2:1)

A solution of 7.5 g (18 mmoles) of 1-[(1,1-dimethylethyl)amino]-3-[2-iodo-5-(trifluoromethyl)phenoxy]-2-propanol, 2.6 ml (23.5 mmoles) of phenylacetylene, 0.063 g (0.09 mmole) of $(Ph_3P)_2PdCl_2$, and 0.034 g (0.179 mmole) of copper (I) iodide in 50 ml of triethylamine was stirred at 25° for 18 hr. An additional 0.3 ml (2.7 mmole) of phenylacetylene was added. The mixture was stirred for 3 hr at 25°. It was diluted with ether and the resulting solution washed with water and brine. The ether solution was dried ($K_2CO_3$) and the solvent evaporated in vacuo. The residue was taken up in MeOH and 0.5 equivalent of fumaric acid added. Ether was added. There was obtained 6.4 g of the crystalline salt. It was recrystallized from MeOH to give 4.5 g (46% yield) of white crystalline 1-[(1,1-dimethylethyl)amino]-3-[(2-phenylethynyl)-5-(trifluoromethyl)phenoxy]-2-propanol (E)-2-butenedioate (2:1), mp 226°–228° C.

What is claimed is:
1. An acetylene of the following formula (I):

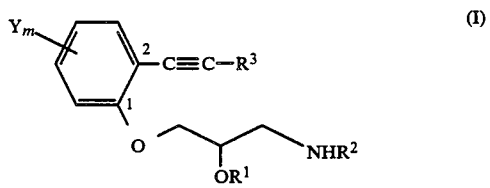

wherein
Y is alkyl, cycloalkyl, fluoro, chloro, bromo, hydroxy, trifluoromethyl, alkoxy, alkylthio, alkenyl, alkynyl, alkenyloxy, alkynyloxy, alkoxyalkyl, alkylthioalkyl, alkanoyl, alkanoyloxy, alkanoylamino, alkanoylaminoalkyl, carboxamido, carboxamidoalkyl, N-alkylcarboxamido, N,N-dialkylcarboxamido, phenyl, or alkylsulfonylamino;
m is 0, 1, 2 or 3;
$R^1$ is hydrogen or alkanoyl;
$R^2$ is iso-propyl, tert-butyl, sec-butyl, phenylethyl, 2-phenyl 1-methylethyl, (substituted phenyl)ethyl or 2-(substituted phenyl)-1-methylethyl wherein the substitution on said phenyl group is independently one or two of fluoro, chloro, bromo, hydroxy, methoxy, ethoxy, methylthio, ethylthio, carboxamido, methyl and ethyl; and
$R^3$ is phenyl or phenyl independently substituted by one, two or three of hydroxy, alkyl, alkoxy, alkylthio, fluoro, chloro, bromo, amino, alkylamino, dialkylamino, alkanoylamino, cyano, carboxamido, N-alkylcarboxamido, N,N-dialkylcarboxamido, N,N-dialkylaminoalkyl and trifluoromethyl, and the pharmaceutically acceptable acid-addition salts thereof.

2. The acetylene of claim 1, wherein

Y is alkyl of about 1 to 6 carbons, cycloalkyl of about 3 to 7 carbons, fluoro, chloro, bromo, hydroxy, trifluoromethyl, alkoxy of about 1 to 6 carbons, alkylthio of about 1 to 6 carbons, alkenyl of about 2 to 6 carbons, alkynyl of about 2 to 6 carbons, alkenyloxy of about 2 to 6 carbons, alkynyloxy of about 2 to 6 carbons, alkoxyalkyl of about 2 to 8 carbons, alkylthioalkyl of about 2 to 8 carbons, alkanoyl of about 2 to 6 carbons, alkanoyloxy of about 2 to 6 carbons, alkanoylamino of about 2 to 6 carbons, alkanoylaminoalkyl of about 3 to 10 carbons, carboxamido, carboxamidoalkyl of about 2 to 6 carbons, N-alkylcarboxamido of about 2 to 6 carbons, N,N-dialkylcarboxamido of about 3 to 11 carbons, phenyl or alkylsulfonylamino of about 1 to 4 carbons;

$R^1$ is hydrogen or alkanoyl of about 2 to 7 carbons; and $R^3$ is phenyl or phenyl independently substituted by one, two or three of hydroxy, alkyl of about 1 to 6 carbons, alkoxy of about 1 to 6 carbons, alkylthio of about 1 to 6 carbons, fluoro, chloro, bromo, amino, alkylamino of about 1 to 4 carbons, dialkylamino of about 2 to 8 carbons; alkanoylamino of about 2 to 6 carbons, cyano, carboxamido, N-alkylcarboxamido of about 2 to 6 carbons, N,N-dialkylcarboxamido of about 3 to 11 carbons, N,N-dialkylaminoalkyl of about 1 to 4 carbons in each alkyl of the dialkyl and about 1 to 6 carbons in the alkylene portion and trifluoromethyl.

3. The acetylene of claim 1, wherein

Y is alkoxy of about 1 to 6 carbons, carboxamido or trifluoromethyl;

m is 0 or 1;

$R^1$ is hydrogen or alkanoyl of about 2 to 7 carbons;

$R^2$ is iso-propyl, tert-butyl, sec-butyl, (substituted phenyl)ethyl or 2-(substituted phenyl)-1-methylethyl wherein the substitution on said phenyl groups is one or two of chloro or methoxy; and $R^3$ is phenyl or phenyl substituted by one or two of alkoxy of about 1 to 6 carbons, chloro, dialkylamino of about 2 to 8 carbons, alkanoylamino of about 2 to 6 carbons, cyano and carboxamido.

4. The acetylene of claim 1, wherein

Y is methoxy, carboxamido or trifluoromethyl;

m is 0 or 1;

$R^1$ is hydrogen or 2,2-dimethylpropanoyl;

$R^2$ is iso-propyl, tert-butyl, (substituted phenyl)ethyl or 2-(substituted phenyl)-1-methylethyl wherein the substitution on said phenyl groups is two methoxy or chloro groups; and $R^3$ is phenyl or phenyl substituted by one or of methoxy, chloro, dimethylamino, acetylamino, cyano and carboxamido.

5. The acetylene of claim 4, wherein Y is at the 4- or 5-position; m is 0 to 1; said substitution on said phenyl groups of $R^2$ are at the 3- and 4-positions; and said substitution on said phenyl group for $R^3$ is at the 3- or 4-positions.

6. The acetylene of claim 1, wherein m is 0; $R^1$ is hydrogen; $R^2$ is tert-butyl; and $R^3$ is phenyl or 4-(dimethylamino)phenyl.

7. The acetylene of claim 1, wherein said acetylene is selected from the group consisting of:

1-[(1,1-dimethylethyl)amino]-3-[2-(phenylethynyl)phenoxy]-2-propanol;

1-[(1,1-dimethylethyl)amino]-3-[2-(phenylethynyl)phenoxy]-2-propyl 2,2-dimethylpropanoate;

1-[(1-methylethyl)amino]-3-[2-(phenylethynyl)phenoxy]-2-propanol;

1-[[2-(3,4-dimethoxyphenyl)ethyl]amino]-3-[2-(phenylethynyl)phenoxy]-2-propanol;

1-[(1,1-dimethylethyl)amino]-3-[5-methoxy-2-(phenylethynyl)phenoxy]-2-propanol;

1-[[2-(3,4-dimethoxyphenyl)ethyl]amino]-3-[5-methoxy-2-(phenylethynyl)phenoxy]-2-propanol;

1-[[2-(3,4-dimethoxyphenyl)ethyl]amino]-3-[2-[[4-(dimethylamino)phenyl]ethynyl]-5-methoxyphenoxy]-2-propanol;

N-[3-[[2-[3-[[2-(3,4-dimethoxyphenyl)ethyl]amino]-2-hydroxypropoxy]-4-methoxyphenyl]ethynyl]phenyl]acetamide;

1-[[2-(3,4-dimethoxyphenyl)ethyl]amino]-3-[5-methoxy-2-[(4-methoxyphenyl)ethynyl]phenoxy]-2-propanol;

1-[[2-(3,4-dichlorophenyl)ethyl]amino]-3-[5-methoxy-2-(phenylethynyl)phenoxy]-2-propanol;

1-[[2-(3,4-dimethoxyphenyl)-1-methylethyl]amino]-3-[5-methoxy-2-(phenylethynyl)phenoxy]-2-propanol;

1-[(1,1-dimethylethyl)amino]-3-[2-(4-chlorophenylethynyl)phenoxy]-2-propanol;

1-[(1,1-dimethylethyl)amino]-3-[2-(4-methoxyphenylethynyl)phenoxy]-2-propanol;

4-[2-[3-[(1,1-dimethylethyl)amino]-2-hydroxypropoxy]phenylethynyl]benzonitrile;

4-[[2-[3-[(1,1-dimethylethyl)amino]-2-hydroxypropoxy]phenyl]ethynyl]benzamide;

1-[(1,1-dimethylethyl)amino]-3-[2-[(4-dimethylaminophenyl)ethynyl]phenoxy-2-propanol;

N-[3-[[2-[3-[(1,1-dimethylethyl)amino]-2-hydroxypropoxy]phenyl]ethynyl]phenyl]acetamide;

4-hydroxy-3-[(1,1-dimethylethyl)amino]propoxy]-3-(phenylethynyl)benzamide; and

1-[(1,1-dimethylethyl)amino]-3-[(2-phenylethynyl)-5-(trifluoromethyl)phenoxy]-2-propanol, and the pharmaceutically acceptable acid-addition salts thereof.

8. The acetylene of claim 1, wherein said acid-addition salt is a salt with an acid selected from the group consisting of hydrochloric, hydrobromic, hydroiodic, perchloric, sulfuric, nitric, a phosphoric, acetic, propionic, glycolic, lactic, pyruvic, malonic, succinic, maleic, fumaric, malic, tartaric, citric, benzoic, cinnamic, mandelic, methanesulfonic, ethanesulfonic, hyroxyethanesulfonic, benzenesulfonic, p-toluene sulfonic, cyclohexanesulfamic, salicyclic, p-aminosalicyclic, 2-phenoxybenzoic, 2-acetoxybenzoic or a salt made with saccharin.

9. The acetylene of claim 1, wherein said acetylene is 1-[(1,1-dimethylethyl)amino]-3-[2-[(4-dimethylaminophenyl)ethynyl)phenoxy]-2-propanol or a pharmaceutically acceptable acid-addition salt thereof.

10. The acetylene of claim 1, wherein $R^3$ is phenyl substituted by one methoxy group.

11. The acetylene of claim 1, wherein $R^3$ is phenyl substituted by two methoxy groups.

12. The acetylene of claim 1, wherein $R^3$ is phenyl substituted by three methoxy groups.

13. The acetylene of claim 1, wherein $R^2$ is tert-butyl.

14. A pharmaceutical composition comprising an acetylene of claim 1 and a pharmaceutically acceptable diluent or carrier.

15. A method of treating hypertension in a mammal which comprises administering to the mammal, the pharmaceutical composition of claim 14.

16. The method of claim 15, wherein said mammal is a human.

17. An oxirane of the following formula (VII):

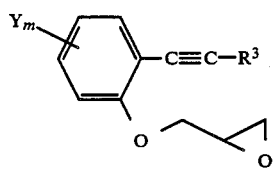

(VII)

wherein
Y is alkyl, cycloalkyl, fluoro, chloro, bromo, hydroxy, trifluoromethyl, alkoxy, alkythio, alkenyl, alkynyl, alkenyloxy, alkynyloxy, alkoxyalkyl, alkylthioalkyl, alkanoyl, alkanoyloxy, alkanoylamino, alkanoylaminoalkyl, carboxamido, carboxamidoalkyl, N-alkylcarboxamido, N,N-dialkylcarboxamido, phenyl, or alkylsulfonylamino;

m is 0, 1, 2, or 3; and $R^3$ is phenyl or phenyl independently substituted by one, two or three of hydroxy, alkyl, alkoxy, alkylthio, fluoro, chloro, bromo, amino, alkylamino, dialkylamino, alkanoylamino, cyano, carboxamido, N-alkylcarboxamido, N,N-dialkylcarboxamido, N,N-dialkylaminoalkyl and trifluoromethyl.

18. The oxirane of claim 17, wherein
Y is alkyl of about 1 to 6 carbons, cycloalkyl of about 3 to 7 carbons, fluoro, chloro, bromo, hydroxy, trifluoromethyl, alkoxy of about 1 to 6 carbons, alkylthio of about 1 to 6 carbons, alkenyl of about 2 to 6 carbons, alkynyl of about 2 to 6 carbons, alkenyloxy of about 2 to 6 carbons, alkynyloxy of about 2 to 6 carbons, alkoxyalkyl of about 2 to 8 carbons, alkylthioalkyl of about 2 to 8 carbons, alkanoyl of about 2 to 6 carbons, alkanoyloxy of about 2 to 6 carbons, alkanoylamino of about 2 to 6 carbons, alkanoylaminoalkyl of about 3 to 10 carbons, carboxamido, carboxamidoalkyl of about 2 to 6 carbons, N-alkylcarboxamido of about 2 to 6 carbons, N,N-dialkylcarboxamido of about 3 to 11 carbons, phenyl or alkylsulfonylamino of about 1 to 4 carbons; and $R^3$ is phenyl or phenyl independently substituted by one, two or three of hydroxy, alkyl of about 1 to 6 carbons, alkoxy of about 1 to 6 carbons, alkylthio of about 1 to 6 carbons, fluoro, chloro, bromo, amino, alkylamino of about 1 to 4 carbons, dialkylamino of about 2 to 8 carbons; N-alkylcarboxamido of about 2 to 6 carbons, N,N-dialkylcarboxamido of about 3 to 11 carbons, N,N-dialkylaminoalkyl of about 1 to 4 carbons in each alkyl of the dialkyl and about 1 to 6 carbons in the alkylene portion and trifluoromethyl.

19. The oxirane of claim 17, wherein
Y is alkoxy of about 1 to 6 carbons, carboxamido or trifluoromethyl;

m is 0 or 1; and $R^3$ is phenyl or phenyl substituted by one or two of alkoxy of about 1 to 6 carbons, chloro, dialkylamino of about 2 to 8 carbons, alkanoylamino of about 2 to 6 carbons, cyano and carboxamido.

20. The oxirane of claim 17, wherein
Y is alkoxy of about 1 to 6 carbons, carboxamido or trifluoro methyl;

m is 0 or 1; and $R^3$ is phenyl or phenyl substituted by one or methoxy, chloro, dimethylamino, acetylamino, cyano and carboxamido.

* * * * *

UNITED STATES PATENT AND TRADEMARK OFFICE
CERTIFICATE OF CORRECTION

PATENT NO. : 4,652,584

DATED : March 24, 1987

INVENTOR(S) : John R. Carson

It is certified that error appears in the above-identified patent and that said Letters Patent is hereby corrected as shown below:

Column 22, line 33, "-2-hydrox-" should read -- -2-hydroxy- --;

Column 22, line 47, "hyroxye-" should read -- hydroxye- --;

Column 22, line 49, "p-aminosalicyclic" should read -- p-aminosalicylic --; and

Column 24, line 15, after " 2 to 8 carbons;", insert -- alkanoylamino of about 2 to 6 carbons, cyano, carboxamido, --.

Signed and Sealed this

Twelfth Day of January, 1988

Attest:

DONALD J. QUIGG

Attesting Officer

Commissioner of Patents and Trademarks